United States Patent [19]

Gay

[11] Patent Number: 4,922,511

[45] Date of Patent: May 1, 1990

[54] DENTAL FILM PACKET

[75] Inventor: George C. Gay, Ontario, N.Y.

[73] Assignee: Eastman Kodak Company, Rochester, N.Y.

[21] Appl. No.: 273,765

[22] Filed: Nov. 21, 1988

[51] Int. Cl.[5] .............................................. A61B 19/04

[52] U.S. Cl. .................................... 378/169; 378/168; 378/182; 378/184

[58] Field of Search ................ 378/168, 169, 182, 184

[56] References Cited

U.S. PATENT DOCUMENTS

| | | | |
|---|---|---|---|
| D. 290,652 | 6/1987 | Simpson | D24/16 |
| D. 291,917 | 9/1987 | Simpson | D24/2 |
| 1,536,341 | 5/1925 | Hodgson | 250/69 |
| 1,537,925 | 5/1925 | Bolin | 250/168 |
| 1,631,497 | 6/1927 | Marler | 250/168 |
| 1,994,579 | 3/1935 | Hodgson | 378/169 |
| 2,084,092 | 6/1937 | Kenney | 250/168 |
| 3,443,093 | 5/1969 | Lindenmuth et al. | 250/069 |
| 4,626,216 | 12/1986 | Strong-Grainger | 433/229 |
| 4,791,657 | 12/1988 | Kirsch et al. | 378/169 |

FOREIGN PATENT DOCUMENTS

| | | | |
|---|---|---|---|
| 0592218 | 7/1925 | France | 378/168 |
| 56-650524 | 11/1981 | Japan . | |

*Primary Examiner*—Carolyn E. Fields
*Assistant Examiner*—David P. Porta
*Attorney, Agent, or Firm*—William C. Dixon

[57] ABSTRACT

A comfort-enhancing improvement upon a known dental film packet having sensitized film and protection opaque sheets enclosed by a light-tight envelope that includes an opposed pair of generally parallel walls covering the sheets, those walls being joined together along facing marginal areas thereof surrounding the sheets so as to define a main body portion and a perimetric edge portion of the envelope. The improvement comprises a deflectable lateral extension of the perimetric edge portion, the extension projecting outwardly therefrom by an amount rendering the edge portion and its extension sufficiently flexible to be readily deflected and folded back around part of the main body portion toward one of said walls, thereby forming a curved resilient cushion where so folded, when the packet is intraorally positioned for a radiographic exposure. In the embodiment illustrated, the extension projects continuously from all of, and is formed as an integral continuation of, the perimetric edge portion, and thus surrounds the main body portion with a pliant cushioning flap.

7 Claims, 3 Drawing Sheets

DENTAL FILM PACKET

BACKGROUND OF THE INVENTION

1. Field of the Invention

The present invention relates generally to intraoral dental radiographic film packets, and particularly to an improvement therein that renders them more ecomfortable for the patient.

2. Description of the Prior Art

The prior art is replete with dental film packets of the type referred to above. Examples may be found in the following documents:

U.S. Pat. No. 1,631,497—Discloses a dental x-ray film package comprising superposed sensitized and protective sheets and a soft, pliable beading that embraces their edges to hold the sheets together and to render the package more comfortable in use; the beading may be of molded rubber or a stretched rubber band cemented in place.

U.S. Pat. No. 3,443,093—Discloses a dental x-ray film package comprising sensitized and protective sheets superposed within a readily openable sealed envelope of substantially uniform overall thickness.

U.S. Pat. No. 4,626,216—Discloses a resilient pad (made of foamed ethylene vinyl acetate) that is folded over, and adhered to, one edge and two corners of a dental x-ray film packet, to enhance comfort and to facilitate positioning in the patient's mouth.

While such film packages and associated pads may have sufficed for their respective purposes, there has remained a persistent need for a dental film packet improvement that would efficiently render the packet more comfortable when operatively positioned inside a patient's mouth. This need has long existed, especially for the particular type of film packet disclosed in the cited U.S. Pat. No. 3,443,093. The squared-off edge defining the perimeter of that packet has been a continuing cause of discomfort for some patients whenever that edge has been pressed into sensitive tissues of the mouth.

A common approach to cushioning that edge has been to attach a soft pad around it, as disclosed, for example, in the cited U.S. Pat. No. 4,626,216. One drawback to adding a cushioning pad has been the resulting increase in overall film package size, which may make it difficult to position the package correctly in the patient's mouth, and may cause stacking and gating problems when loaded into commonly used film packet dispensing devices. Another drawback of the typical cushioning pad has been that the open-cell, or foamed, material used therein to enhance its cushioning effect absorbs patient saliva, which may be contaminated with contagious viruses.

Although dental x-ray film packets of the type disclosed in U.S. Pat. No. 3,443,093 have been widely used for more than twenty years, the long-recognized need to ameliorate discomfort felt by some patients, in a practical and efficient manner, without adversely increasing the packet's in-use size, and without employing highly porous, saliva-absorbing materials, remains unresolved.

SUMMARY OF THE INVENTION

A primary object of this invention has been to meet the foregoing need for such a comfort-enhancing film packet improvement. Another object has been to do so in a totally reliable, yet practical and economical, manner. Those and other objects have been achieved by the invention herein disclosed and claimed.

This invention finds utility as a comfort-enhancing improvement upon a known intraoral dental radiographic film packet having sensitized film and protective opaque sheets enclosed by a light-tight envelope that includes an opposed pair of generally parallel walls covering the sheets, those walls being joined together along facing marginal areas thereof surrounding the sheets so as to define a main body portion and a perimetric edge portion of the envelope. The improvement comprises a deflectable lateral extension of the perimetric edge portion, the extension projecting outwardly therefrom by an amount rendering the extended edge portion sufficiently flexible to be readily deflected when the packet is operatively positioned inside a patient's mouth, thereby cushioning the impact of the envelope perimetric edge. In the preferred embodiment of this invention, the extension projects outwardly from, and continuously along, all of the perimetric edge portion.

This invention, and its objects and advantages, will become more apparent in the detailed description of the preferred embodiment presented hereinbelow.

BRIEF DESCRIPTION OF THE DRAWINGS

In the detailed description of the preferred embodiment of this invention presented below, reference is made to the accompanying drawings, wherein like reference characters denote like elements, and wherein.

DESCRIPTION OF THE PREFERRED EMBODIMENT

Because certain parts of intraoral dental radiographic film packets are well known, the following description is directed in particular to those elements forming, cooperating directly with, or relating to, this invention. Elements not specifically shown or described herein are selectable from those known in the relevant art.

Figure 1:
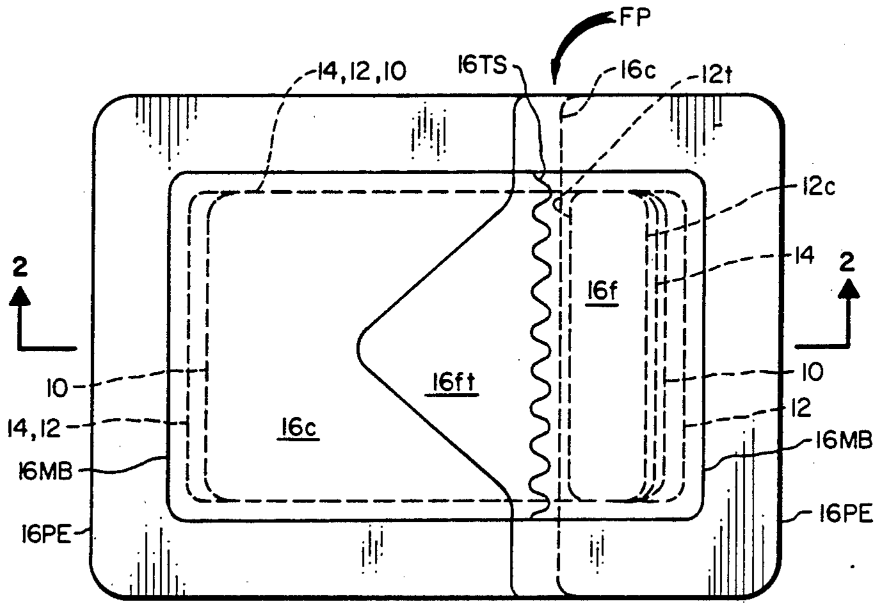
FIG. 1 (PRIOR ART)
FIG. 1 is a top-plan view of an intraoral dental radiographic film packet as known in the prior art, and to which the film packet improvement of this invention is directed.
Figure 2:
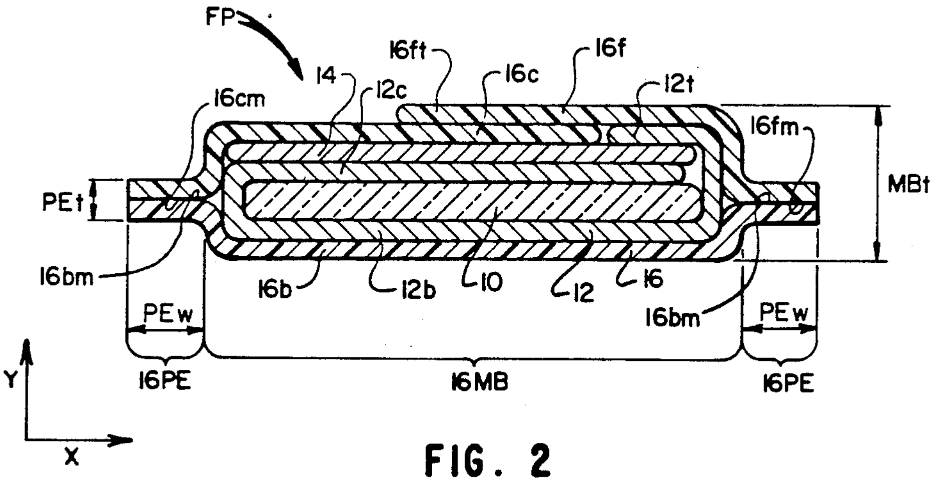
FIG. 2 (PRIOR ART)
FIG. 2 is a cross-sectional elevation of the known packet depicted in FIG. 1, taken along line 2—2 therein and showing principal components thereof exaggerated in thickness for clarity of illustration.

FIGS. 1 and 2 illustrate an intraoral dental radiographic film packet of a type known in the prior art, e.g., as disclosed in the aforementioned U.S. Pat. No. 3,443,093, and to which the film packet improvement of this invention is described. The known packet, designated generally by the letters FP, comprises a sheet of x-ray film 10 having a sensitive emulsion on one or both sides (as is well known in the art); a folded black paper wrapper 12; a sheet of metal foil 14 substantially the same shape and size as the film sheet 10; and an enclosing envelope 16, preferably plastic, within which the foregoing components are arranged as shown and sealed. As is well known, the envelope 16 may be made of a duplex plastic sheet, i.e., a sheet of white plastic on the outside laminated to a sheet of black plastic on the inside. The plastic preferred for the envelope is polyvinylchloride, although polyethylene, Pliofilm, cryovac, or other plastic films or combinations of plastics might also be used. The white outside surface of the envelope may be matte, glossy, or embossed. The metal foil sheet 14 preferably is made of lead, but any metal that absorbs x-rays satisfactorily for dental radiographic purposes may be employed.

In the assembled film packet, as shown in FIG. 2, the paper wrapper 12 comprises a base section *12b* underlying film sheet 10, a folded-over cover section *12c* overlying film sheet 10, and a folded-over tab section *12t* overlying the right-hand end portions of film sheet 10 and cover section *12c*. It will be seen that metal foil sheet 14 lies between cover section *12c* and tab section *12t*. The plastic envelope 16 comprises a bottom wall *16b* underlying the paper wrapper base section *12b*, a cover section 16c overlying the metal foil sheet 14, and a flap section *16f* overlying both the paper wrapper tab section *12t* and the envelope cover section *16c*. Cover section *16c* and flap section *16f* together form the top wall of the envelope. As shown in FIG. 1, the left-hand end portion of envelope flap section *16f* is triangular in shape, to form a tab end *16ft* of the flap section. Flap section *16f* is tack-sealed to cover section *16c*, transversely of the envelope as indicated by the undulated line 16TS. The envelope bottom wall *16b* includes an upward-facing marginal area *16bm* which is sealed to an opposing downward-facing marginal area 16cm of cover section *16c* and an opposing downward-facing marginal area *16fm* of flap section *16f*. The seal may be provided in any suitable manner, e.g., by heat, ultrasonics, or an adhesive. To open the packet for processing film sheet 10 after its exposure, the technician first grasps the unsealed tab end *16ft* of flap section *16f* and then pulls the flap section upwardly, so as to break the transverse seal 16TS and rip open the seal between marginal areas *16fm* and *16bm*. With the envelope thus opened, the technician then grasps paper wrapper tab section *12t* and pulls paper wrapper 12 out of the envelope with film sheet 10 riding between wrapper base and cover sections *12b* and *12c*.

With the envelope bottom wall *16b* joined to the top wall cover and flap sections *16c* and *16f* along their opposing marginal areas as described, the envelope may be viewed as comprising a main body portion 16MB surrounded by a perimetric edge portion 16PE, as shown most clearly in FIG. 2. It will be seen that the squared-off peripheral edge of perimetric edge portion 16PE includes relatively sharp top and bottom corners, which have caused discomfort when pressed against sensitive oral tissues in some patients. The present invention provides an efficient and reliable means for ameliorating such discomfort.

As a comfort-enhancing improvement upon a film packet of the type thus far described, this invention comprises a deflectable lateral extension of the envelope perimetric edge portion 16PE, the extension projecting outwardly therefrom by an amount rendering the edge portion and its extension sufficiently flexible to be readily deflected when operatively positioned inside a patient's mouth, thereby cushioning the impact of the relatively sharply cornered envelope edge.

Figure 3:
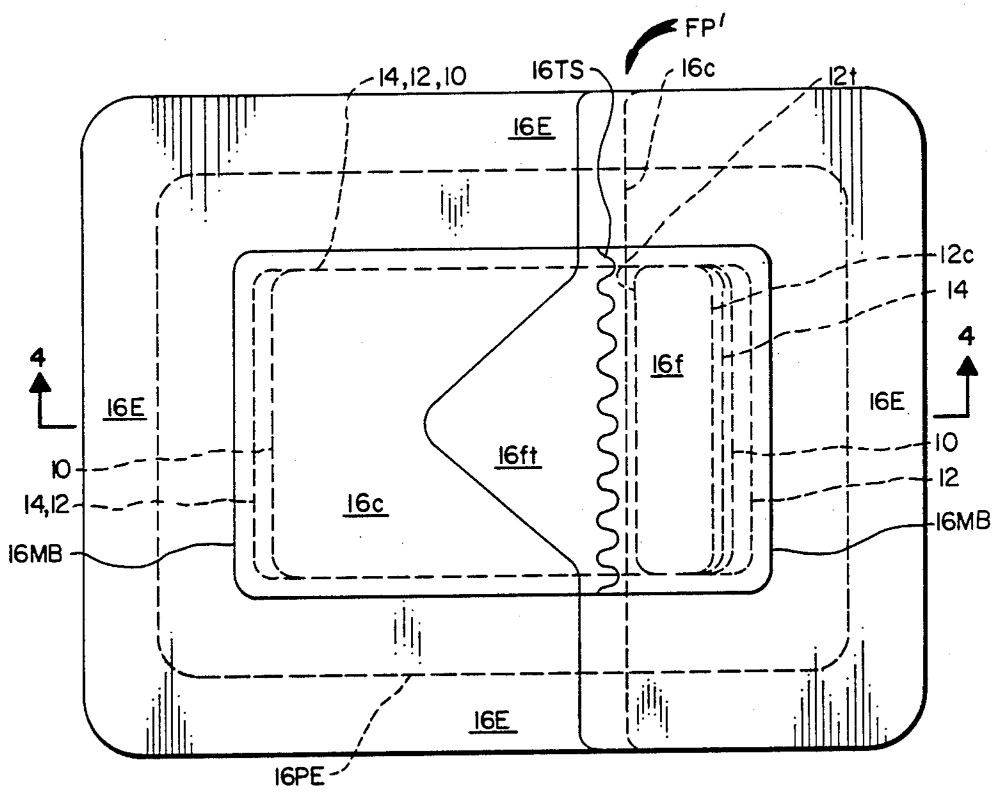
FIG. 3 is a top-plan view similar to FIG. 1 but illustrating the film packet therein as improved by the preferred embodiment of this invention, and as disposed in its normally flat condition.

In accordance with the preferred embodiment, and as shown most clearly in FIG. 3, the extension 16E is continuous around all of, and thus surrounds, the perimetric edge portion 16PE. It should be understood, however, that this invention also contemplates alternative embodiments (not shown) wherein the extension may be discontinuous along, or project from only part(s) of, the perimetric edge portion. For example, such an extension could be provided only along selected portions of the envelope sides and/or ends.

Figure 4:
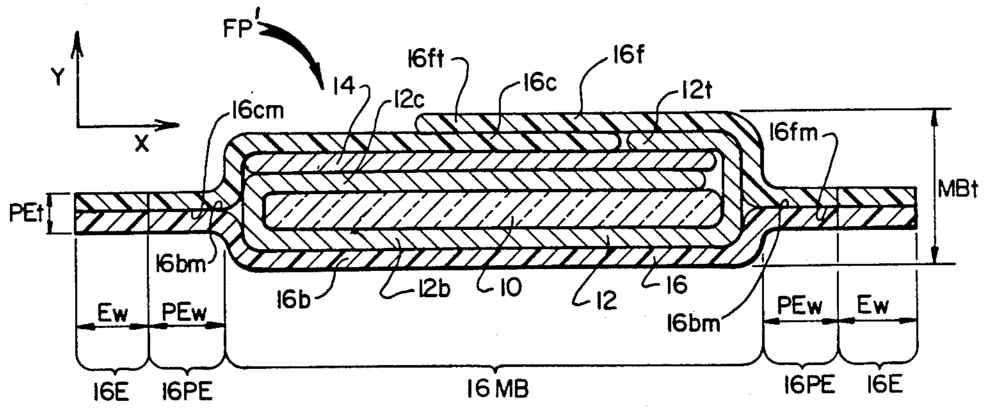
FIG. 4 is a cross-sectional elevation of the improved packet of FIG. 3, taken along line 4—4 therein and showing its principal components exaggerated in thickness for clarity.

As viewed in FIGS. 2 and 4, the perimetric edge portion 16PE, from which extension 16E projects, has an edge portion thickness PEt, measured in a first direction Y perpendicular to the envelope bottom and top walls, and an edge portion width PEw, measured in a second direction X parallel with the envelope walls. Also as viewed in FIGS. 2 and 4, the envelope main body portion 16MB has an overall thickness MBt, measured in first direction Y; and as seen in FIG. 4, the extension 16E projects laterally outward beyond the perimetric edge portion 16PE by an amount Ew measured in second direction X.

The extension amount, or width, Ew may be defined variously in terms of the perimetric edge portion thickness PEt, the main body portion overall thickness MBt, or/and the perimetric edge portion width PEw. Generally speaking, it has been found that the amount Ew should be approximately 20 times the edge portion thickness PEt. It also has been noted that Ew should be at least 2 times, but not more than 4 times, and preferably about 3 times, the body portion overall thickness MBt. It also has been observed that the width Ew should be at least 3 times, but not more than 7 times, and preferably between 4 and 6 times, the edge portion width PEw. Depending upon dimensional and material variations that might occur among differing film packets of this type, the foregoing relationships advantageously may be combined by defining the extension amount, or width, Ew as being approximately 20 times the edge portion thickness PEt, but no less than the greater of 3 times the edge portion width PEw and 2 times the overall thickness MBt, and no more than the lesser of 7 times the edge portion width PEw and 4 times the overall thickness MBt.

In a number of film packet samples analyzed, the envelope main body portion overall thickness MBt, as measured in first direction Y, ranged from about 0.056 inches (1.422 mm) to about 0.061 inches (1.549 mm), with a mean of about 0.058 inches (1.483 mm); the envelope perimetric edge portion thickness PEt, as measured in first direction Y, ranged from about 0.006 inches (0.157 mm) to about 0.012 inches (0.310 mm), with a mean of about 0.010 inches (0.246 mm); and the envelope perimetric edge portion width PEw, as measured in second direction X, averaged about 0.035 inches (0.889 mm). Preferably, for packets having such dimensions, the envelope extension width Ew, as measured in second direction X, should range only from about 0.140 inches (3.556 mm) to about 0.210 inches (5.334 mm).

To facilitate understanding of this invention as an improvement upon a known dental film packet, FIG. 4 illustrates the envelope extension 16E as though it might comprise an additional part abutting the envelope perimetric edge portion 16PE. Although conceivably the extension could be a separate piece joined to the edge portion, in the preferred embodiment as successfully produced and tested, the extension is conveniently formed as an integral lateral continuation of the edge portion itself. That is, the envelope bottom and top walls 16*b* and 16*c*, 16*f* are simply made larger than before, to provide the desired extension width Ew, and their thus-enlarged upward-and downward-facing marginal areas are sealed together as before. Accordingly, FIG. 3 indicates only by phantom outline the periphery of the initial, unextended perimetric edge portion 16PE.

Figure 5:
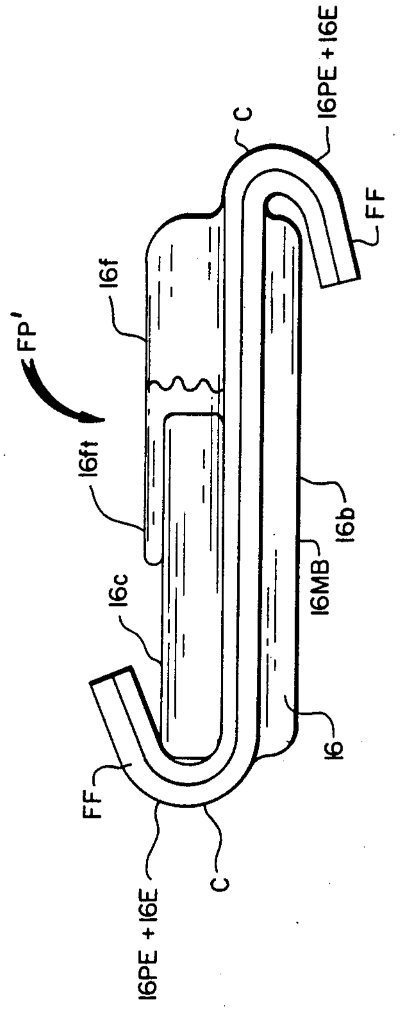
FIG. 5 is a side elevation of the improved packet shown in FIGS. 3 and 4, illustrating the pliant marginal flap portions thereof as they might be folded back upon its main body portion.

FIG. 5 illustrates the improved film packet FP′ with its integrally extended perimetric edge portion appearing as a pair of oppositely projecting flexible flaps FF that have been deflected from their initial plane (shown in FIG. 4) and folded back upon the envelope main body portion 16MB. Although, for purposes of illustration, FIG. 5 shows the improved packet FP′ with its left flap folded over and its right flap folded under the main body portion, it should be understood that either one or both of the flaps FF might be folded either way when the packet is appropriately positioned inside a patient's mouth. The curved portion C where each flap FF is folded, either way, around a body portion end provides an inherently resilient cushion to enhance patient comfort when that end of the packet is pressed against sensitive oral tissues. While not shown in FIG. 5, the same condition prevails when the enlarged lateral margins (top and bottom as viewed in FIG. 3) of the extended perimetric edge portion are similarly deflected and folded (again, either way) around the body portion sides, thereby providing the same cushioning effect regardless of the packet's orientation when operatively positioned inside the mouth. It should be noted that, during use, when the flexible flaps formed by extending the perimetric edge portion in accordance with this invention are deflected and folded back around the body portion ends or sides, toward the body portion top or bottom, to assume their cushioning configuration (such as that illustrated in FIG. 5), the overall length or width of the packet is not increased to an extent that would interfere with optimum positioning of the packet for the desired radiographic exposure.

It has been found that such an extension of the known packet's perimetric edge portion has proven effective in cushioning sensitive oral tissues from any discomfort that might otherwise be felt by some patients. The film packet improvement of this invention has thus successfully fulfilled the aforementioned widespread, long-recognized, but hiterto-unresolved need for a more comfortable intraoral dental radiographic film packet, and has done so without adversely increasing the packet's in-use size or resorting to a highly porous, saliva-absorbing material.

The present invention has now been described in detail with particular reference to its preferred embodiment illustrated herein. It will be understood, however, that variations and modifications can be effected within the spirit and scope of this invention.

I claim:

1. A comfort-enhancing improvement upon an intraoral dental radiographic film packet having sensitized film and protective opaque sheets enclosed by a light-tight envelope that includes an opposed pair of generally parallel walls covering the sheets, said walls being joined togehter along facing marginal areas thereof surrounding the sheets, thereby defining a main body portion and a perimetric edge portion of the envelope, said improvement comprising a deflectable lateral extension of substantially all of said perimetric edge portion, said extension projecting outwardly therefrom by an amount rendering said substantially all of said edge portion and said extension thereof sufficiently flexible to be readily deflected, so as to form a comfort-enhancing yieldable cushion where so deflected, when the packet is operatively positioned for effecting an intraoral radiographic exposure, said main body portion of the envelope having an overall thickness as measured perpendicular to said walls, said amount by which said extension projects outwardly from said substantially all of said perimetric edge portion being at least twice said overall thickness.

2. A comfort-enhancing improvement as claimed in claim 1 wherein said amount is no greater than four times said overall thickness.

3. A comfort-enhancing improvement as claimed in claim 2 wherein said amount is approximately three times said overall thickness.

4. A comfort-enhancing improvement upon an intraoral dental radiographic film packet having sensitized film and protective opaque sheets enclosed by a light-tight envelope that includes an opposed pair of generally parallel walls covering the sheets, said walls being joined together along facing marginal areas thereof surrounding the sheets, thereby defining a main body portion and a perimetric edge portion of the envelope, said improvement comprising a deflectable lateral extension of substantially all of said perimetric edge portion, said extension projecting outwardly therefrom by an amount rendering said substantially all of said edge portion and said extension thereof sufficiently flexible to be readily deflected, so as to form a comfort-enhancing yieldable cushion where so deflected, when the packet is operatively positioned for effecting an intraoral radiographic exposure, said perimetric edge portion of the envelope having an edge portion thickness as measured perpendicular to said walls, said amount by which said extension projects outwardly from said substantially all of said perimetric edge portion being approximately twenty times said edge portion thickness.

5. A comfort-enhancing improvement upon an intraoral dental radiographic film packet having sensitized film and protective opaque sheets enclosed by a light-tight envelope that includes an opposed pair of generally parallel walls covering the sheets, said walls being joined together along facing marginal areas thereof surrounding the sheets, thereby defining a main body portion and a perimetric edge portion of the envelope, said improvement comprising a deflectable lateral extension of substantially all of said perimetric edge portion, said extension projecting outwardly therefrom by an amount rendering said substantially all of said edge portion and said extension thereof sufficiently flexible to be readily deflected, so as to form a comfort-enhancing yieldable cushion where so deflected, when the packet is operatively positioned for effecting an intraoral radiographic exposure, said main body portion of the envelope having an overall thickness dimension as measured in a first direction perpendicular to said walls, said perimetric edge portion of the envelope having an edge portion thickness dimension as measured in said first direction and an edge portion width dimension as measured in a second direction parallel with said walls, said extension projecting outwardly from said substantially all of said perimetric edge portion in said second direction, said amount by which said extension so projects being approximately twenty times said edge portion thickness but no less than twice said overall thickness.

6. A comfort-enhancing improvement as claimed in claim 5 wherein said amount is no greater than four times said overall thickness.

7. A comfort-enhancing improvement upon an intraoral dental radiographic film packet having sensitized film and protective opaque sheets enclosed by a light-tight envelope that includes an opposed pair of generally parallel walls covering the sheets, said walls being joined together along facing marginal areas thereof surrounding the sheets, thereby defining a main body portion and a perimetric edge portion of the envelope, said improvement comprising a deflectable lateral extension of substantially all of said perimetric edge portion, said extension projecting outwardly therefrom by an amount rendering said substantially all of said edge portion and said extension thereof sufficiently flexible to be readily deflected, so as to form a comfort-enhancing yieldable cushion where so deflected, when the packet is operatively positioned for effecting an intraoral radiographic exposure, said main body portion of the envelope having an overall thickness ranging from about 0.056 inches (1.422 mm) to about 0.061 inches (1.549 mm), said perimetric edge portion of the envelope having an edge portion thickness ranging from about 0.006 inches (0.157 mm) to about 0.012 inches (0.310 mm) and an edge portion width of approximately 0.035 inches (0.889 mm), said amount by which said extension projects outwardly from said substantially all of said perimetric edge portion ranging from about 0.140 inches (3.556 mm) to about 0.210 inches (5.334 mm).

* * * * *